(12) United States Patent
Hewitt

(10) Patent No.: US 7,369,226 B1
(45) Date of Patent: May 6, 2008

(54) OPTICAL SENSOR DEVICE HAVING VARIABLE OPTICAL PATH LENGTH

(76) Inventor: Joseph P. Hewitt, 14911 251st Pl. SE., Issaquah, WA (US) 98027

( * ) Notice: Subject to any disclaimer, the term of this patent is extended or adjusted under 35 U.S.C. 154(b) by 0 days.

(21) Appl. No.: 11/002,021

(22) Filed: Dec. 1, 2004

(51) Int. Cl.
*G01N 21/01* (2006.01)
(52) U.S. Cl. .................................. 356/244; 356/246
(58) Field of Classification Search ................ 356/244, 356/338, 440, 442, 246, 335–343
See application file for complete search history.

(56) References Cited

U.S. PATENT DOCUMENTS

| | | | |
|---|---|---|---|
| 6,175,420 B1 * | 1/2001 | Barry et al. ................. | 356/436 |
| 6,324,343 B1 * | 11/2001 | Yasuda ........................ | 396/87 |
| 6,809,826 B2 * | 10/2004 | Robertson ................... | 356/440 |

* cited by examiner

*Primary Examiner*—Gregory J. Toatley, Jr.
*Assistant Examiner*—Tri Ton

(57) ABSTRACT

An optical sensor is provided with an adjustable and variable optical path length (OPL). The optical sensor can be used in conjunction with a flow cell for ultraviolet (UV) absorbance measurements. On opposite sides of the flow cell, optical windows are installed in cylindrical window holders and held in place by window retainers. The distance between opposing faces of the optical windows defines the OPL. A fine pitch, close tolerance thread is machined on the outside of the window holders. This thread mates with a thread machined on an inside wall of a mounting ring. Rotation of the window holder and attached optics housing extends or retracts the window and window holder assembly, thereby providing the variable OPL. The OPL can be ascertained by examining external visual linear and/or rotational indicators on the sensor device.

26 Claims, 3 Drawing Sheets

10mm OPL

0mm OPL

OPTICAL SENSOR DEVICE HAVING VARIABLE OPTICAL PATH LENGTH

TECHNICAL FIELD

This disclosure relates generally to optical sensor devices, and in particular but not exclusively, relates to an optical monitoring device, such as an inline flow cell device usable for ultraviolet (UV) absorbance measurements and having an adjustable optical path length.

BACKGROUND INFORMATION

The biotechnology industry has progressed over the years from relatively simple lab benches to highly complex manufacturing processes. The industry has adopted manufacturing techniques and equipment from various existing processes and modified such processes to meet certain distinct uses. For example, in-line optical monitoring instrumentation (originally developed for applications ranging from brewing to chemical process) has been modified for use in the biotechnology field.

The biotechnology industry has evolved considerably with the development of new processing equipment and techniques to improve yields, ensure regulatory compliance, and increase production capabilities. However, optical monitoring instrumentation, which is an integral part of nearly every production process in the biotechnology industry, has not kept pace with this trend. Current in-line optical instrumentation is functionally no different than the instrumentation adopted from other industries many years ago.

Most modern biotechnology manufacturing facilities use three distinct inline optical monitoring technologies to help monitor and control their processes. Near infrared (NIR) absorption sensors are used primarily to monitor cell density in bioreactors and to measure certain concentrations in various separation stages, such as centrifugation, perfusion, and filtration. Scattered light turbidmeters are used to detect low concentrations solids carryover in the purified centrate or filtrate streams from these separation processes. Further downstream, ultraviolet (UV) absorption sensors are used to measure protein concentrations on the outlet of chromatography columns.

The protein concentration measurement using UV absorption sensors is one of the primary control parameters in the entire manufacturing process. A UV absorption sensor typically comprises an inline flow cell with quartz or sapphire windows and lamp and detector assemblies mounted on opposing sides of the flow cell. The distance between the windows provides the optical path length (OPL). The protein concentration can be measured or otherwise determined by directing light through the windows, and then determining the amount of light absorbed by the material (e.g., protein) that is present between the windows.

A variable that is available to adjust the range of measurement is the OPL. Increasing the OPL improves sensitivity but reduces the maximum measurement range. Decreasing the OPL has the inverse effect. This need for changes in the OPL can be driven by a process change that results in higher protein concentrations or the switch to an entirely different product, for instance, which happens quite frequently in process development and manufacturing facilities.

To achieve a desired OPL, current online UV sensors employ a combination of optical windows of different thickness with flow cells of varying internal dimensions, thereby obtaining a range of discrete OPLs available for a given line size. Typically, available OPLs range from 1-10 mm in 1-2.5 mm increments for a given UV sensor. Regardless of the particular OPL for a given UV sensor, the commonality is that the OPL is fixed for any given sensor.

One of the drawbacks of current UV sensors is that even minor OPL changes require time-consuming and sometimes expensive hardware changes. For instance, to change the OPL requires, at a minimum, replacement of the optical windows, and quite frequently, replacement of the flow cell as well. To replace both optical windows and the flow cell can cost $2000-$2500. More importantly, if the specific required flow cells are unavailable from a vendor or other supplier, this switch can delay processing for 4-6 weeks or other significant amount of time.

As an illustration with the currently available UV sensors, a combination of three different flow cells and up to six different windows might be required to achieve all available optical path lengths from 1-10 mm for a given line size. In order to maintain maximum flexibility, a process development facility, vendor, or other entity might have to stock all of these parts. Furthermore, if a manufacturing facility needs to inventory all possible spares (which is typical), the manufacturing facility would usually have to stock numerous flow cells and numerous window combinations to cover all of their applications. Maintaining this inventory also has additional associated costs based on the requirement of traceability of materials. This procedure is not just a matter of grabbing a flow cell off of a shelf, but rather also involves locating and recording all appropriate paperwork and certifications.

Existing UV sensors also have significant drawbacks in precision/accuracy. With traditional hardware, the accuracy of the OPL is determined by three parameters: the distance between the window seats on the flow cell as well as the thickness of each of the two optical windows. Using tightly controlled manufacturing methods, current manufacturers have been able to maintain the tolerances on each of these dimensions to ±0.05 mm. This means that a cumulative error of ±0.15 mm is still within tolerance. Probably the most common optical path length for chromatography applications is 1 mm, which means that the stated tolerances could result in an error of ±15%. The worst-case scenario would have the readings on redundant UV sensors deviating from one another by 30% (one +15%, one −15%), and still being within tolerance. Typically, when manufacturers use redundant sensors, the sensor readings have to be within a certain tolerance of one another (usually 5-10%) or the run will have to be terminated. Because of the OPL deviations, several manufacturers have had to modify their sensor readings with a "fudge factor" to keep the readings within tolerance. These deviations are impractical in situations where a precise determination of OPL is desirable.

On the UV sensors currently used in the industry, there is no external indication of optical path length. This makes it difficult, if not impossible, to determine the actual OPL of an installed UV sensor without removing the flow cell from the process, and in many cases, completely disassembling it. This problem has led to many instances of faulty calibration based on incorrect assumptions about optical path length. Numerous situations exist where users have assumed that they are operating with a certain OPL (for instance 2 mm), when in reality, the manufacturer has provided a UV sensor with a different OPL (for instance 1 mm OPL). Also, because the windows for different optical path length are identical in appearance except for small variations in length (sometimes as small as 0.5 mm, for instance), it is extremely easy for users to mismatch windows when re-assembling flow cells after cleaning or service, again resulting in incorrect OPLs. Since there is no external indication of optical path length, this type of problem can take many hours to resolve. Because many of the line sizes used are too small to allow use of a ball mill or other mechanism to directly measure the OPL, the only way to reliably determine OPL is to completely disassemble the flow cell, measure the window thicknesses with calipers, and then consult with the factory to determine what OPL that window combination and flow cell will yield. Again, these hours are often inside of a controlled clean room. In the worst-case scenario, the manufacturer actually makes product using the improperly configured sensor to control cuts.

Other costs are associated with current UV sensors having fixed OPLs. For instance, there is also the additional cost of bringing the UV sensor back into a clean environment and re-sterilizing after an OPL change has been made. Clearly therefore, current UV sensors having fixed OPLs are impractical in many situations.

BRIEF SUMMARY OF THE INVENTION

According to one aspect, a system includes a flow cell body that defines an interior channel. A first optical window has a first surface positionable within the interior channel of the flow cell body. A second optical window has a second surface positionable within the interior channel of the flow cell body. The first and second surfaces face each other and define an optical path length (OPL). A first window holder is movably coupled to the flow cell body and is coupled to the first optical window. A second window holder is coupled to the flow cell body and is coupled to the second optical window, wherein at least the first window holder is movable relative to the flow cell body to cause a corresponding change in the OPL. An indicator indicates the change in the OPL.

BRIEF DESCRIPTION OF THE SEVERAL VIEWS OF THE DRAWINGS

Non-limiting and non-exhaustive embodiments are described with reference to the following figures, wherein like reference numerals refer to like parts throughout the various views unless otherwise specified or unless the context is otherwise.

DETAILED DESCRIPTION

Figure 1:
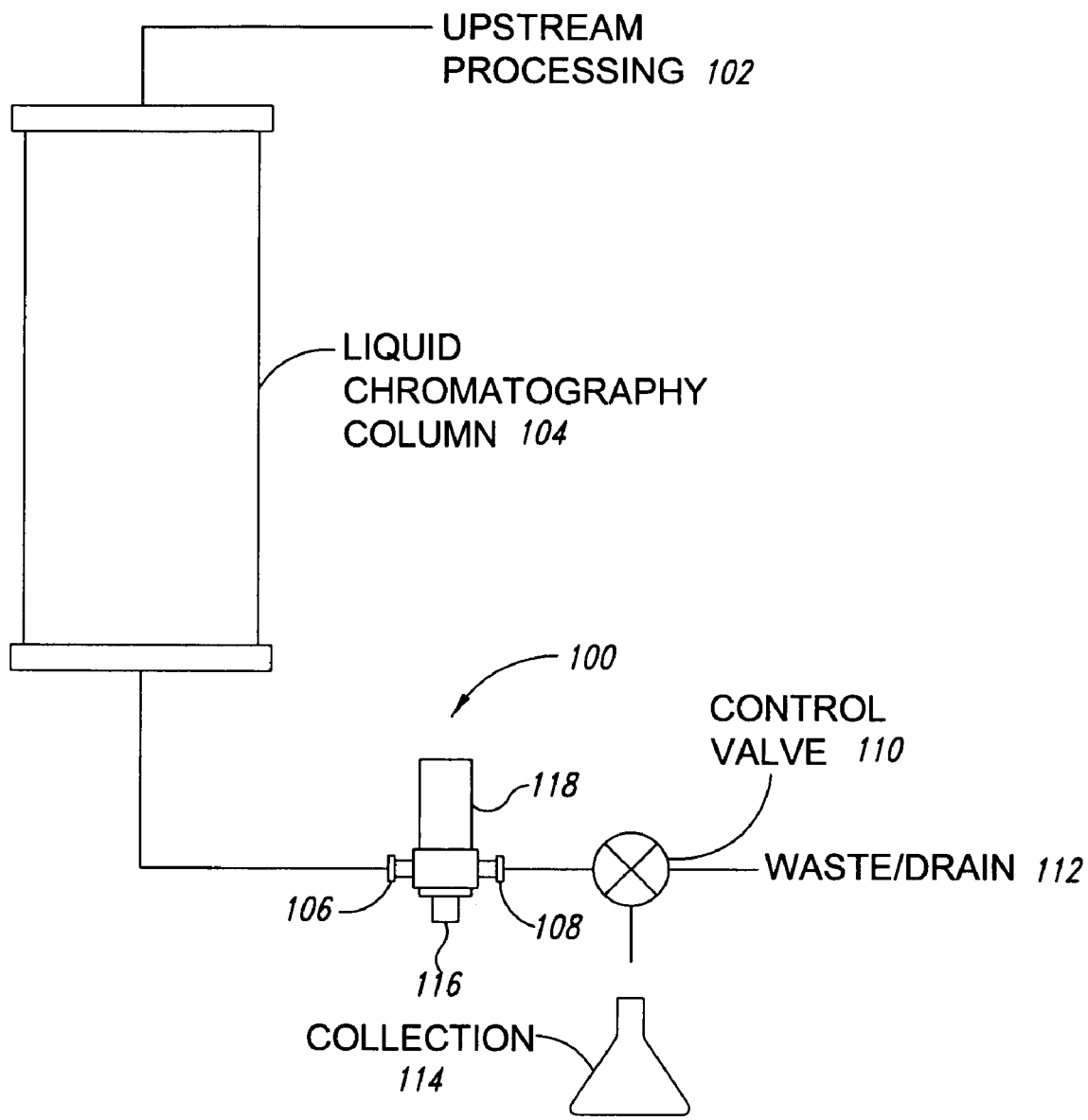
FIG. 1 is a block diagram illustrating a possible use of one embodiment of an optical sensor device.

In the following description, numerous specific details are given to provide a thorough understanding of embodiments. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless the context requires otherwise, throughout the specification and claims which follow, the word "comprise" and variations thereof, such as, "comprises" and "comprising" are to be construed in an open, inclusive sense, that is as "including, but not limited to."

The headings provided herein are for convenience only and do not interpret the scope or meaning of the claimed invention.

As an overview, one embodiment provides an optical sensor having an adjustable OPL. The adjustability thus provides the optical sensor with a variable OPL that overcomes the drawbacks of current sensors discussed above. In an embodiment, the optical sensor can be used in conjunction with a flow cell. On opposite sides of the flow cell, optical windows are installed in cylindrical window holders and held in place by window retainers. A fine pitch, close tolerance thread is machined on the outside of the window holders (or the mechanical bodies to which the window holders attached). This thread mates with a thread machined on an inside wall of a mounting ring. Rotation of the window holder and attached optics housing extends or retracts the window and window holder assembly.

In an example and non-limiting embodiment, a 1 mm thread pitch is provided so that each full revolution of the assembly will increase or decrease the OPL by exactly 1 mm, thereby allowing very precise adjustment of the window spacing. Visual indicators, such as rotational and/or linear indicators, can be provided on the optical sensor so that its user can readily determine the OPL without having to disconnect the optical sensor from the process or to disassemble the optical sensor. For instance, an external linear index can be marked on the optical sensor to allow the user to readily verify the OPL without having to use measurement calipers.

For purposes of illustration, an embodiment of the optical sensor is described herein in the context of a biotechnology implementation. It is appreciated that embodiments can also be provided for chemical, brewery, pulp and paper, fermentation, pharmaceutical, winery, and/or other sectors of industry and/or research fields.

FIG. 1 illustrates an example use of an embodiment of an optical sensor device 100. In this particular implementation, the sensor device 100 comprises a UV absorbance sensor, and it is appreciated that sensor devices 100 of other embodiments need not necessarily be configured for UV absorbance measurement.

The sensor device 100 of FIG. 1 is installed inline in an ongoing process. This ongoing process (such as a protein purification process, for instance) involves upstream processing 102, which feeds liquid and particulates into an inlet of a liquid chromatography column 104 or other suitable molecular separation device. The liquid chromatography column 104 has an outlet that is coupled to a first flow cell section 106 of the sensor device 100. The sensor device 100 has a second flow cell section 108 that is coupled to a control valve 110. The control valve 110 separates the output from the liquid chromatography column 104 into a waste/drain unit 112 and a collection unit 114. For example, the collection unit 114 may receive desired proteins that are generated by the illustrated process.

In an embodiment, a lamp 116 can be included with or coupled to the sensor device 100 so as to provide the UV source (or other light source) for the absorbance measurements. An analysis system 118 can be included with or coupled to the sensor device 100 across from the lamp 116. The analysis system 118 can include, for example, photodetectors, electronics, hardware, and software to analyze the received light (after an amount of the original transmitted light has been absorbed by the matter flowing through the flow cell sections 106 and 108) and to determine optical absorbance therefrom and/or to perform other functions. For the sake of simplicity, the lamp 116 and analysis system 116 is illustrated symbolically in FIG. 1 (rather than great detail) and will not be described in further detail herein.

Figure 2:
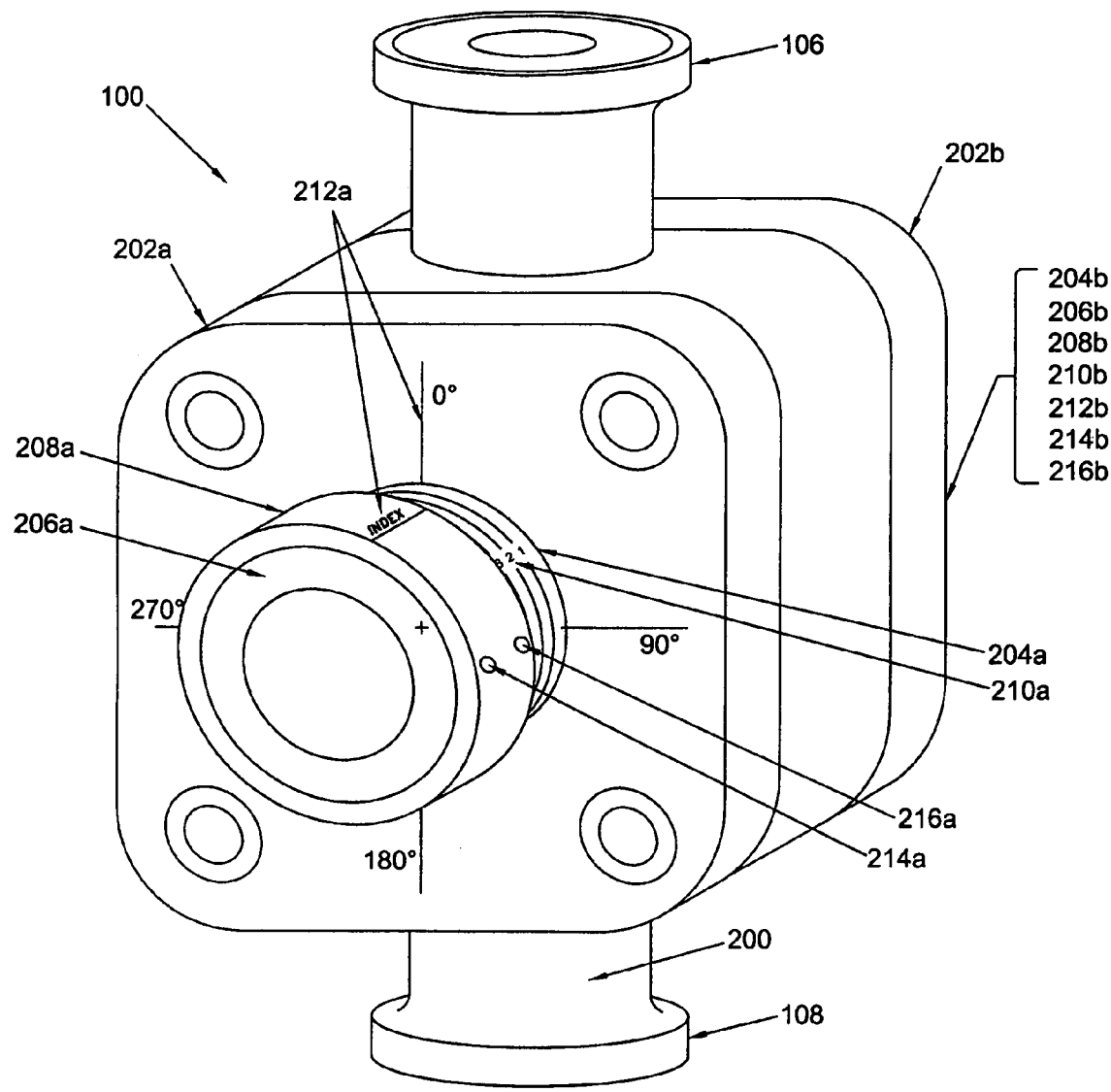
FIG. 2 is perspective view of an embodiment of the sensor device.

FIG. 2 is a perspective view of an embodiment of the sensor device 100. The flow cell sections 106 and 108 can comprise industry standard fluid processing connections, for instance, to allow tight coupling with tubes, pipes, or hoses. The flow cell sections 106 and 108 are integrated together as part of a flow cell body 200 that defines an interior channel.

Mounting rings 202a and 202b are coupled to opposing sides of the flow cell body 200. Hereinafter, for sake of simplicity of explanation, illustration, and notation, the reference labels "a" and "b" are used to denote symmetric components in the overall sensor device 100. Where appropriate, each symmetric component will be described in the singular, so as to avoid undue redundancy if the other symmetric component is also described. The mounting ring 202a includes a threaded opening to receive a threaded portion 204a of a window holder 206a. An indexing ring 208a is coupled to the window holder 206a.

According to one embodiment, the threaded portion 204a of the window holder 206a is machined or otherwise formed with close tolerance male thread, such as a 1 mm thread pitch, which mates with a similarly pitched female thread that is machined in an inside wall of the mounting ring 202a. Thus, a complete revolution of the window holder 206a will result in a displacement of 1 mm. By lining up index marks after each full rotation, the OPL can be precisely adjusted and determined.

In an embodiment, a visual linear indicator 210a is provided on the mounting ring 202a to indicate a value of the OPL. In particular for a specific embodiment, the linear indicator 210a comprises graduated numerical indicators (such as millimeter indicators) that are marked on the cylindrical extension of the mounting ring 202a. Thus, each full revolution of the window holder 206a will result in the index ring 208a aligning to a corresponding one of the mm indicators. A similar linear indicator can be provided for the other mounting ring 202b.

There are different techniques to configure the linear indicators of the mounting rings 202a and 202b. In one example, a 1 mm indication on both linear indicators can indicate that the OPL has a length of 2 mm (e.g., a 1 mm contribution from the displacement of each window holder 206a and 206b). In another embodiment, the linear indicators can be positioned on the window holders 206a and 206b in such a manner that a 1 mm reading on both indicators represents a 1 mm OPL (and not a 2 mm OPL). In yet another embodiment, a linear indicator can be provided for only one of the mounting rings. Various configurations are possible.

According to one embodiment a visual rotational indicator 212a can be provided on the mounting ring 202a (and/or on the other mounting ring 202b). Such a rotational indicator 212a can display, for instance, an angular displacement of the window holder 206a. Thus, an indexing mark (such as another rotational indicator 212a, which is symbolically or physically represented as "INDEX" in FIG. 2, or other indexing mark that is present on the indexing ring 208a) can be aligned to any rotational position between 0 degrees and 360 degrees, as the window holder 206a is rotated. By counting the number of rotations and then aligning to such rotational indicators 212a and 212b, for both respective window holders 206a and 206b, the precise OPL adjustment can be performed if the thread pitch is known.

The linear indicator 210a and the rotational indicator 212a of an embodiment are visual indicators in that the user can visually inspect/monitor such indicators to readily determine the OPL, without having to disconnect or disassemble the sensor device 100. In another embodiment, a measurement caliper (not shown) can be used to measure displacement between certain reference points/landmarks on the sensor device 100, thereby determining the OPL from the displacement measured by the caliper. In yet another embodiment, electromechanical devices (such as wireless position sensors) can be used to determine the displacement and hence the OPL.

Figures 3, 4:
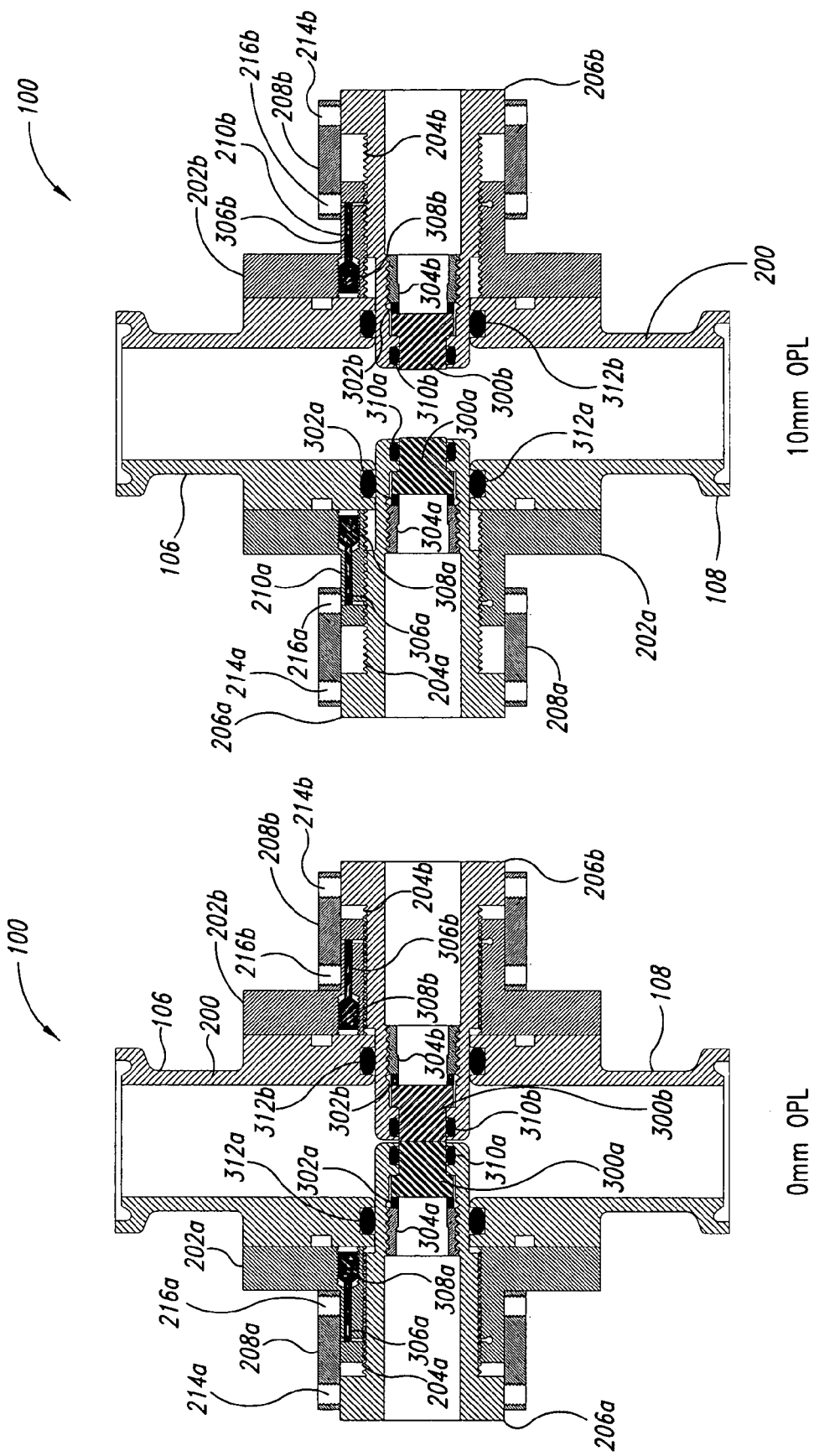
FIG. 3 is a first side sectional view of an embodiment of the sensor device.
FIG. 4 is a second side sectional view of an embodiment of the sensor device.

FIG. 3 is a first side sectional view that shows in detail other components an embodiment of the sensor device 100. The window holder 206a is generally cylindrical in shape and has an internal chamber that is shaped to accommodate (at its distal end) an optical window 300a. Within the interior channel of the flow cell body 200, the optical window 300a faces an optical window 300b that is housed in the opposing window holder 206b. The distance between the opposing surfaces of the optical windows 300a and 300b is the OPL. In FIG. 3, the zero (0) OPL is shown, wherein the opposing surfaces of the optical windows 300a and 300b touch each other.

In one embodiment, the optical windows 300a and 300b can be made from sapphire. In another embodiment, the optical windows 300a and 300b can be made from quartz. Other materials having the desired optical characteristics can be used.

A packing washer 302a is placed between the optical window 300a and a window retainer ring 304a. The packing washer 302a serves to protect the optical window from damage when the window retainer ring 304a is tightened to secure the optical window 300a. The packing washer 302a can be made from any suitable material having the desired compressability or other desirable physical characteristic(s). An example material is a molded polytetrafluoroethylene material such as Teflon®. The window retainer ring 304a serves to hold the optical window 300a in place at the distal end of the window holder 206a.

O-rings 310a and 312a serve as seals to prevent liquid, flowing inside of the flow cell body 200, from entering the interior of the window holder 206a or the interior of mounting ring 202a and then contaminating electronics equipment coupled thereto. O-ring 310a provides a liquid tight seal between optical window 300a and window holder 206a. O-ring 312a provides a liquid tight seal between window holder 206a and flow cell body 200. Both seals can utilize proven industry standard shaft seal designs, for instance. The O-rings 310a and 312a can be made from any suitable material having the desired sealing performance and meeting industry standards for product contact. An example material is ethylene-propylene-diene-monomer (EPDM) rubber.

According to one embodiment, the sensor device 100 includes a backlash prevention rod 306a. The backlash prevention rod 306a is held in place in the mounting ring 202a via a set screw 308a. This backlash prevention rod 306a provides some binding in the mating threads of the mounting ring 202a and the window holder 204a. This prevents any "slop" or other ancillary movement in the threads when the direction of threading is reversed.

FIG. 4 is a second side sectional view of an embodiment of the sensor device 100. This particular view illustrates linear displacement of the window holders 206a and 206b (such as by application of a rotational force to these window holders to cause rotational movement along their respective threaded portions 204a and 204b) from an inside position towards an external position. Thus, rotation of the window holders 206a and 206b to this external position has resulted in a change (increase) in OPL between the opposing surfaces of the optical windows 300a and 300b. For instance, the illustrated position in FIG. 4 can represent an OPL of 10 mm.

In an embodiment, movement along the threaded portions 204a and 204b can be performed by having the user grip or otherwise hold the indexing rings 208a and 208b, and then applying the requisite rotational force. The rotational force can be applied clockwise or counterclockwise as needed to extend or retract the window holders 206a and 206b.

Therefore to summarize, an embodiment of the sensor device 100 has been described in which the window shaft assemblies are threaded into the mounting rings 202a and 202b on each side of the flow cell body 200. For initial set up, the first step is to set the backlash prevention rods 306a and 306b. After this step is complete, the window holders 206a and 206b are screwed in, until the faces of the two optical windows 300a and 300b meet in the center of the flow cell body 200. This will establish an absolute zero for the OPL (see, e.g., FIG. 3). With the window holders 206a and 206b in this position, the indexing rings 208a and 208b are installed flush to the mounting rings 202a and 202b, respectively, and permanently fixed to the respective window holders 206a and 206b or optics housing assemblies using set screws 214a and 214b (also shown in FIG. 2).

The window holder assemblies can then be rotated to retract the window shafts and set the desired OPL. When the exact OPL is achieved, set screws 216a and 216b (also shown in FIG. 2) can be used to lock the window holders 206a and 206b in place. The OPL can be quickly and accurately verified by using calipers, for example, to measure the exact distance between the indexing ring 208a and the mounting ring 202a on each side of the flow cell body 200 (or using some other landmarks on the sensor device 100). In addition, the mounting ring 202a and window holder assembly will be rotationally indexed to one another at the zero point, enabling precise OPL adjustments in 1 mm increments to be achieved by lining up the index marks after each rotation, for example if a 1 mm thread pitch is used. Finally, a simple linear index (such as the linear indicator 210a) can be included to provide a means of quickly verifying the OPL of a sensor device 100 without calipers.

The adjustable OPL of an embodiment of the sensor device 100 offers the ability to set an absolute zero point for the OPL that compensates for variations due to machining tolerances of the individual components. At the factory, for example, the window holders 206a and 206b are adjusted until the opposing optical windows 300a and 300b meet in the center of the flow cell body 100. This represents a true zero point for the OPL. With the optical windows 300a and 300b in this position, the external indexing rings 208a and 208b are affixed to the window holders 206a and 206b using the set screws 214a and 214b, respectively, to mark the zero point. Any adjustment or movement of the optical windows 300a and 300b after this time will move the indexing rings 208a and 208b (on the outside of the flow cell body 200) by an equal amount. By using National Institute of Standards and Technology (NIST) traceable calipers to measure the distance that the indexing ring 208a or 208b has traveled from the zero point, the user can accurately determine (and validate) the actual optical path length from the exterior of the flow cell body 200. The user interface (which is part of the analysis system 118 of FIG. 1) provides a means of entering the actual OPL, which can then be used to calculate optical density with great precision. Outputs of the analysis system 118 are reported in optical density (OD) as calculated using the actual OPL entered by the user The various embodiments of the sensor device 100 are depicted in the figures using certain shapes and relative sizes for the components. It is understood that such shapes and sizes of these components can vary from one embodiment to another, and are presented herein solely for purposes of explanation and illustration and are not to be construed as limitations. Example details (such as illustrative and non-limiting shapes and dimensions) of one or more embodiments of the sensor device 100 are disclosed in co-pending U.S. Provisional Patent Application Ser. No. 60/648,369 entitled "OPTICAL SENSOR DEVICE," filed Jan. 28, 2005, with inventors Joseph P. Hewitt and Paul C. Williams, assigned to the same assignee as the present application, and incorporated herein by reference in its entirety.

The following is a non-exclusive and non-limiting list of advantages provided by an embodiment of the sensor device 100 having an adjustable OPL:

a) Greater Flexibility—OPL can be easily adjusted and validated in the field, without disassembling the sensor device 100, purchasing new optical windows, or replacing the flow cell.

b) Improved Accuracy—OPL zero point can be adjusted at the factory to compensate for slight variations in flow cell dimensions. Where currently available sensors offer OPL tolerances of ±0.15 mm, tolerances of ±0.05 mm or better are achievable with one embodiment. For a sensor device with 1 mm OPL, this represents an improvement in accuracy from ±15% to ±5%. The backlash prevention rod 306a helps ensure this accuracy.

c) External Indication of OPL—OPL setting is clearly visible on the outside of the sensor device 100. OPL can be measured and validated with calipers without removing the sensor flow cell from the process.

d) Minimized Inventory—Only one flow cell design can be used for each line size, and a single window size will work in all applications. This approach will minimize inventory requirements for both the manufacturer and the end users.

e) Improved Seal Design—The shaft seals that will be utilized have been proven in thousands of sanitary applications and are much more widely accepted in these applications than the hybrid face seal utilized for window sealing in most of the sensors currently available.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The above description of illustrated embodiments, including what is described in the Abstract, is not intended to be exhaustive or to limit the invention to the precise forms disclosed. While specific embodiments and examples are described herein for illustrative purposes, various equivalent modifications are possible within the scope of the invention and can be made without deviating from the spirit and scope of the invention.

For example, while one embodiment has been described in the context of a biotechnology industry application, it is appreciated that other embodiments can be provided for other uses where it is desirable to have an adjustable OPL. Moreover, different materials can be used for the optical windows alternatively or additionally to sapphire or quartz. Examples include glass, plastic, molded polytetrafluoroethylene such as Teflon®, or any other material having the desired optical characteristics. Light sources (lamps) and photodetectors different than those specifically described herein may also be used in other embodiments.

Except where otherwise indicated or apparent from context, the various components of the sensor device 100 can be made of metal or thermoplastic materials. Examples of metals that might be used include, but are not limited to, stainless steel, brass, copper, or other suitable metals or alloys having the desired physical characteristics. Examples of suitable thermoplastics include, but are not limited to, polyvinylidene fluoride (PVDF) such as Kynar®, polyetheretherkeytone (PEEK), polytetrafluoroethyene (PTFE) such as Teflon®, or other suitable thermoplastics having the desired physical characteristic(s).

These and other modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. A system, comprising:
   a flow cell body that defines an interior channel;
   a first optical window having a first surface positionable within the interior channel of the flow cell body;
   a second optical window having a second surface positionable within the interior channel of the flow cell body, the first and second surfaces facing each other and defining an optical path length (OPL) therebetween;
   a first window holder movably coupled to the flow cell body and being coupled to the first optical window;
   a second window holder coupled to the flow cell body and being coupled to the second optical window, wherein at least the first window holder is movable relative to the flow cell body to cause a corresponding change in the OPL; and
   an indicator to indicate the change in the OPL.

2. The system of claim 1 wherein the second window holder is movably coupled to the flow cell body and wherein both the first and second window holders are movable relative to the flow cell body to cause the corresponding change in the OPL.

3. The system of claim 1, further comprising first and second mounting rings coupled to the flow cell body and which are respectively coupled to the first and second window holders, at least the first mounting ring including a threaded portion to rotationally mate with a threaded portion of the first window holder, wherein the first window holder is movably coupled to the flow cell body via rotational movement between the threaded portions of the first window holder and the first mounting ring.

4. The system of claim 3 wherein the threaded portions of the first window holder and the first mounting ring include a thread pitch, the thread pitch corresponding to the change in OPL in a manner that a thread displacement generated by a full rotational movement between the threaded portions is equal to the change in OPL.

5. The system of claim 3 wherein the second mounting ring includes a threaded portion to rotationally mate with a threaded portion of the second window holder, wherein the second window holder is movably coupled to the flow cell body via rotational movement between the threaded portions of the second window holder and the second mounting ring to cause at least part of the change in the OPL.

6. The system of claim 3 wherein the indicator to indicate the change in the OPL includes a visual indicator positioned on the first mounting ring.

7. The system of claim 6 wherein the visual indicator includes a graduated linear numerical indicator placed on the first mounting ring and being indicative of a change in the OPL per rotation about the threaded portions.

8. The system of claim 3 wherein the indicator to indicate the change in the OPL includes a rotational indicator.

9. The system of claim 3, further comprising an indexing ring coupled to the first window holder, wherein the indicator to indicate the change in the OPL includes a measurable displacement distance, between the indexing ring and a landmark, that corresponds to the OPL.

10. The system of claim 9 wherein the landmark includes the first mounting ring.

11. The system of claim 3, further comprising a backlash prevention rod assembly coupled to the first mounting ring to provide additional binding between the threaded portions of the first mounting ring and the first window holder.

12. The system of claim 11 wherein the backlash prevention rod assembly comprises a set screw coupled to a backlash prevention rod.

13. The system of claim 1 wherein a substantially absolute zero OPL is obtained if the first window holder is moved to a position where the first surface of the first optical window touches the second surface of the second optical window.

14. The system of claim 1, further comprising:
    a lamp positioned adjacent to the first window holder in a manner to direct a light through the first optical window, across the OPL, and through the second optical window; and
    an analysis system positioned adjacent to the second window holder to receive the light that has been directed through the second optical window by the lamp and to provide an optical absorbance determination based on the received light.

15. An apparatus usable for determining optical absorbance associated with a process flow, the apparatus comprising:
    first and second mounting elements;
    a first window holder coupled to the first mounting element;
    a second window holder coupled to the second mounting element;
    first and second optical windows respectively coupled to the first and second window holders, a distance between the coupled first and second optical windows defining an optical path length (OPL);
    an adjustment feature to allow the OPL to be changed while connected to the process flow; and
    an indicator to indicate the change in OPL.

16. The apparatus of claim 15 wherein at least the first window holder is movably coupled to the first mounting element in a manner that a displacement of the first window holder caused by the adjustment feature causes a corresponding change in the OPL.

17. The apparatus of claim 15 wherein both the first and second window holders are movably coupled to the respective first and second mounting elements, and wherein the adjustment feature includes threaded portions, the first and second window holders having threaded portions that rotatably engage threaded portions of the respective first and second mounting rings in a manner that a corresponding displacement about such threaded portions causes a substantially identical displacement of the OPL.

18. The apparatus of claim 17 wherein the indicator includes a graduated linear numerical indicator, respectively associated with each of the first and second window holders, that represents the change in the OPL, the linear numerical indicator being placed on the first and second mounting elements in a manner that each complete rotational movement along the threaded portions corresponds to a graduation indicated by the linear numerical indicators.

19. The apparatus of claim 17, further comprising a rotational indicator representative of rotation about the threaded portions and which can be correlated to the change in OPL.

20. The apparatus of claim 15, further comprising a pair of backlash rod assemblies to provide improved binding between first and second mounting elements and the first and second window holders, respectively, if the first and second window holders are displaced by the adjustment feature to change the OPL.

21. The apparatus of claim 15 wherein the adjustment feature is usable to move either one or both of the first and second window holders to a position where the first and second optical windows touch to define a substantially absolute zero OPL.

22. The apparatus of claim 15, further comprising:
first and second indexing elements respectively coupled to the first and second window holders, the adjustment feature being usable to change positions of the first and second window holders to generate displacements between the first and second indexing elements and respective landmarks, the generated displacements being substantially equal to the OPL; and
two pairs of set screws, a first screw of each pair being used to couple that screws associated indexing element to that indexing element's associated window holder, a second screw of each pair being used to lock that associated window holder in place.

23. A system usable for a process flow, the system comprising:
means for mounting a pair of optical windows to a body, a distance between the pair of optical windows defining an optical path length (OPL);
means for changing the OPL while in the process flow, wherein the means for changing the OPL includes threaded means for receiving a rotational force to linearly displace the pair of optical windows from a first OPL position to a second OPL position;
and means for indicating the change in the OPL.

24. The system of claim 23 wherein the means for changing the OPL includes means for setting a substantially absolute zero OPL, and wherein the means for indicating the change in the OPL includes a means for externally determining a new OPL based on the substantially absolute zero OPL that was set.

25. A method, comprising:
placing an optical sensor device in a process flow;
setting an optical path length (OPL) between optical windows of the sensor device;
changing the OPL from the set OPL while the sensor device remains in the process flow, wherein changing the OPL includes applying a rotational force to the sensor device to cause a corresponding linear change in the OPL, the rotational force causing a rotational displacement that corresponds to a linear displacement of the OPL; and
providing an indication of the change in the OPL while the sensor device remains in the process flow.

26. The method of claim 25, further comprising:
setting the OPL to a substantially absolute zero position; and
determining the OPL using the set substantially absolute position, if the OPL is subsequently changed.

* * * * *